(12) United States Patent
Zucca et al.

(10) Patent No.: US 7,884,130 B2
(45) Date of Patent: Feb. 8, 2011

(54) GAMMA-UNDECENOLACTONE, METHOD FOR THE PREPARATION AND USE THEREOF FOR COSMETICS AND IN THE FORM OF FOOD ADDITIVES

(75) Inventors: Joseph Zucca, Grasse (FR); Jean Mane, Grasse (FR)

(73) Assignee: V. Mane Fils, Bar-sur-Loup (FR)

( * ) Notice: Subject to any disclaimer, the term of this patent is extended or adjusted under 35 U.S.C. 154(b) by 755 days.

(21) Appl. No.: 11/666,987

(22) PCT Filed: Nov. 2, 2005

(86) PCT No.: PCT/FR2005/002729

§ 371 (c)(1),
(2), (4) Date: May 31, 2007

(87) PCT Pub. No.: WO2006/048550

PCT Pub. Date: May 11, 2006

(65) Prior Publication Data

US 2008/0125345 A1    May 29, 2008

(30) Foreign Application Priority Data

Nov. 3, 2004  (FR) .................................. 04 11721

(51) Int. Cl.
*A61K 31/341* (2006.01)
*C07D 307/33* (2006.01)

(52) U.S. Cl. ...................................... 514/473; 549/326

(58) Field of Classification Search ................. 514/473; 549/326
See application file for complete search history.

(56) References Cited

U.S. PATENT DOCUMENTS

| 4,950,607 | A | | 8/1990 | Cardillo et al. | |
|---|---|---|---|---|---|
| 4,960,597 | A | * | 10/1990 | Farbood et al. | 426/3 |
| 5,457,036 | A | * | 10/1995 | Han et al. | 435/126 |

FOREIGN PATENT DOCUMENTS

| DE | 4126997 | 2/1993 |
|---|---|---|
| EP | 0258993 | 3/1988 |
| EP | 0519481 | 12/1992 |

OTHER PUBLICATIONS

Wilson et al., J. Org. Chem. (1988), vol. 53(20), pp. 4682-4693.*
ISR dated Feb. 3, 2006 from PCT/FR2005/002729.

* cited by examiner

*Primary Examiner*—Taofiq A Solola
(74) *Attorney, Agent, or Firm*—Young & Thompson

(57) ABSTRACT

The invention relates to a gamma-undecenolactone of formula (i), wherein a lactonic cycle can carry an unsaturation between carbon No. 2 and carbon No. 3 and is preferably saturated, RI is a possibly substituted $C_7$ alkenyl or alkynyl group having at least one unsaturation, and preferably RI is an $CH_2=CH-CH_2-CH_2-CH_2-CH_2-CH_2$ group, the gamma-undecenolactone contains an asymetric carbon in position 4 having (R) or (S) configuration. The biosynthesis of the gamma-undecenolactone and the use thereon for perfumery and for a food flavoring agent are also disclosed.

7 Claims, No Drawings

GAMMA-UNDECENOLACTONE, METHOD FOR THE PREPARATION AND USE THEREOF FOR COSMETICS AND IN THE FORM OF FOOD ADDITIVES

The present invention relates to a new lactone, gamma-undecenolactone; to the synthesis thereof via the biological process, in particular the stereoselective synthesis of each of its (R) or (S) isomers and to the uses thereof, in particular in the food and perfumery sector.

"Natural" products are increasingly appreciated by the general public and, as a result, industries that use aromatic or odorant compounds concentrate their efforts on the development of "natural" aromatizing substances and preparations. Only substances that have been identified in nature can aspire to this label; they are therefore currently produced either from plants or from microorganisms; the latter are increasingly used, biotechnological processes now making it possible to synthesize natural molecules at reasonable expense. This is the case of gamma-lactones.

Gamma-lactones are aromatic molecules that constitute the aroma and the flavor of many natural products. For example, gamma-heptalactone is known for its hazelnut or caramel aroma and taste, gamma-nonalactone has a fatty, creamy, or coconut aroma; gamma-decalactone and gamma-undecalactone have a peach or apricot aroma and taste.

Gamma-lactones exist naturally, in their two enantiomeric forms (R) and (S), the (R) enantiomer being, however, predominant.

Gamma-lactones can be produced synthetically, or by biosynthesis by means of microorganisms. Thus, EP 371 568 describes a process for producing gamma-lactones by means of microorganisms that are acceptable for preparing food products, such as, in particular, *Saccharomyces cerevisiae*, *Debaromyces hansenii* or *Candida boidinii*.

U.S. Pat. No. 5,112,803 indicates that gamma-octalactone, and in particular its (R) and (S) optical isomers, can be used to form butter aromas and flavors, and describes a process for increasing the aroma or the flavor of materials that can be consumed, by adding significant amounts of optically active gamma-octalactones, and a mixture of various compounds which are by-products of the biological process for obtaining gamma-octalactones, described in said patent. The process described in U.S. Pat. No. 5,112,803 indicates that, using caprylic acid, it is possible to obtain the two (R) and (S) isomers of gamma-octalactone by biosynthesis using strains of the genus *Syncephalastratum* sp. or *Mortierella* sp.; however, this process is not enantioselective.

Gamma-lactones are of great value in the food flavoring industry and in the perfumery industry, and real industrial high stakes are involved in the production of products that have different organoleptic nuances.

The object of the present invention is to propose a new gamma-lactone, gamma-undecenolactone, which has aromatic and gustative properties comparable to those of known gamma-lactones, but different from the latter, in particular pineapple and passion fruit aromas and flavors.

It is known that the chirality of volatile molecules can induce differences in terms of olfactory perception, and that the optical isomers of gamma-lactones do not all have the same organoleptic notes: there is therefore a considerable advantage in producing a specific optical isomer of a gamma-lactone, in particular if this production is carried out according to a process that is at least as efficient, or even more efficient, than in the prior art and at a competitive cost.

Another object of the invention is therefore to propose a process for the biological synthesis of gamma-undecenolactone that is efficient and economical, and in particular a process for the stereoselective synthesis of each of the (R) and (S) optical isomers of gamma-undecenolactone.

The gamma-undecenolactone in accordance with the invention corresponds to formula (I):

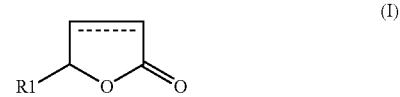

in which the lactone ring can bear an unsaturation between carbon No. 2 and carbon No. 3, and in which R1 is a $C_7$ alkenyl or alkynyl group bearing at least one unsaturation, including one $C_{10}$-$C_{11}$ alkenic unsaturation, said R1 group being optionally substituted.

According to a preferred embodiment of the invention, R1 comprises a single unsaturation. Very preferably, this unsaturation is an alkenic unsaturation.

According to another embodiment of the invention, R1 comprises several unsaturations, including one $C_{10}$ alkenic unsaturation and at least one other alkenic unsaturation on a carbon other than $C_7$.

According to a specific embodiment of the invention, R1 is an optionally substituted alkene group having 7 carbon atoms, bearing a single unsaturation located at $C_{10}$-$C_{11}$.

According to another preferred embodiment of the invention, R1 is not substituted with a halogen atom, in particular bromine or chlorine.

According to a preferred embodiment of the invention, R1 is a $C_7H_{13}$ group, preferably the group $CH_2$=CH—$CH_2$—$CH_2$—$CH_2$—$CH_2$—$CH_2$—, and the lactone ring is saturated.

According to another embodiment of the invention, R1 comprises a single alkynic unsaturation, preferably on carbon 10.

The term "substituted alkenyl or alkynyl" is intended to mean an alkenyl or alkynyl in which at least one carbon bears at least one substituent group. The term "substituent group" is intended to mean in particular a hydroxyl group, a keto group, a thiol group, an alkyl group or an alkenyl group.

The gamma-undecenolactone according to the invention contains an asymmetric carbon in position 4 and can be in the (R) or (S) configuration.

The invention relates to both the (R)-gamma-undecenolactone and the (S)-gamma-undecenolactone, and the mixture, in any proportions whatsoever, of these two optical isomers, in particular the racemic mixture.

The invention also relates to the biological preparation of the gamma-undecenolactone of formula (I), and in particular its biosynthesis via the microbial pathway, from at least one substrate, in particular undecylenic acid or one of its esters, preferably methyl or ethyl ester, using a microbial culture of a strain chosen from those that allow hydroxylation of the substrate, in particular at $C_4$.

This preparation comprises the following steps:
a) selecting an appropriate strain,
b) culturing said strain in an appropriate culture medium, said culturing being optionally preceded by a step consisting in preculturing the strain,
c) adding a substrate that can be converted into gamma-undecenolactone of formula (I),
d) bioconverting the substrate to gamma-undecenolactone of formula (I),
e) recovering the gamma-undecenolactone of formula (I) thus produced.

The appropriate microbial strains, targeted in step a) for the biosynthesis of the gamma-undecenolactone according to the invention, are those that allow specific hydroxylation of the substrate, in particular at $C_4$.

When the product resulting from the biosynthesis is for use in the food industry, the food-grade strains are of course preferred. Among the strains that allow stereo-selective hydroxylation, mention may in particular be made of the strains of the genus *Aspergillus* sp., *Penicillium* sp., *Mucor* sp., *Mortierella* sp. Since the strains all belong to microorganism class 1, and since some are food strains, their use does not pose any specific problem either for the industrial production of lactone or for its possible use in food products.

According to a specific embodiment of the invention, the strain used is of the genus *Aspergillus* sp., preferably *Aspergillus oryzae*, of which mention may be made of the following collections of strains: *Aspergillus oryzae* DSMZ 1861, *Aspergillus oryzae* DSMZ 1864, *Aspergillus oryzae* DSMZ 1147, *Aspergillus oryzae* DSMZ 63303, *Aspergillus oryzae* CBS 570.65, *Aspergillus oryzae* CBS 819.72, *Aspergillus oryzae* CBS 110.27, *Aspergillus oryzae* VMF 88093.

Among them, *Aspergillus oryzae* DSMZ 1861 and *Aspergillus oryzae* CBS 110.27 are preferred.

According to another specific embodiment, the strain used is of the genus *Mortierella* sp., of which mention may be made of the following collections of species: *Mortierella isabellina* DSMZ 1414, *Mortierella isabellina* CBS 100559, *Mortierella isabellina* CBS 221.29, *Mortierella isabellina* CBS 194.28, *Mortierella isabellina* CBS 208.32, *Mortierella isabellina* CBS 224.35, *Mortierella isabellina* CBS 560.63, *Mortierella isabellina* CBS 167.80, *Mortierella isabellina* CBS 493.83, *Mortierella isabellina* CBS 309.93, *Mortierella isabellina* CBS 250.95, *Mortierella isabellina* CBS 109075, *Mortierella ramanniana* CBS 112.08, *Mortierella ramanniana* CBS 219.47, *Mortierella ramanniana* CBS 243.58, *Mortierella ramanniana* CBS 478.63, *Mortierella ramanniana* CBS 852.72, *Mortierella ramanniana* CBS 366.95, *Mortierella ramanniana* CBS 101226.

Among them, the *Mortierella isabellina* strains will be preferred, in particular *Mortierella isabellina* DSMZ 1414, *Mortierella isabellina* CBS 100559 and *Mortierella isabellina* CBS 221.29.

In fact, the inventors have noted that, surprisingly and unexpectedly, the use of a strain of the genus *Aspergillus* sp. results in the selective production of (R)-gamma-undecenolactone, and that the use of a strain of the genus *Mortierella* sp. results in the selective production of (S)-gamma-undecenolactone.

According to one embodiment of the invention, *Yarrowia lipolytica* strains are excluded from the invention since they are not capable of bringing about hydroxylation at $C_4$. Advantageously, all strains which are not capable of specifically and stereoselectively producing hydroxylation at $C_4$ are excluded from the present invention.

Without wishing to be bound by any theory, it can be envisioned that the conditions for culturing the strains could be of importance in the stereoselectivity observed, and also in the quantitative aspect of the bioconversion.

The culture targeted in step b) of the process according to the invention comprises the preparation of a culture, preferably a semi-concentrated culture, of the strains, for example by cell amplification, in an appropriate culture medium. This culture may be preceded by a preculture of the strains in a first culture medium more suitable for the first steps of multiplication of the strain.

The culture conditions used in the stereoselective process of the invention should be such that they result in the production of a mycelium which exhibits swellings filled with inclusions (with peroxysomes in particular). According to the preferred embodiment of the invention, the cell culture prepared has a "compot" mycelium composed of compartmentalized filaments with no conidiospores and exhibiting bulging structures, filled with these inclusions (peroxysomes). The culture conditions should in fact be particularly appropriate for preventing sporulation of the mycelium.

Moreover, the inventors have been able to note that the physiological state of the mycelium, obtained in particular due to the use of the culture conditions described in the present application (compartmentalized mycelium comprising swellings and bulges filled with inclusions, in particular with peroxysomes) could have a considerable influence on the reaction yield and would make it possible to obtain yields greater than those of the prior art. The physiological state of the mycelium could also have an influence on the stereoselectivity of the reaction.

Thus, according to a preferred embodiment of the invention, step b) of the process of the invention is a step consisting in culturing the strain in an appropriate culture medium for obtaining a compartmentalized mycelium comprising swellings and bulges filled with inclusions, in particular with peroxysomes. Advantageously, the culture medium used according to the invention does not contain peptone. Preferably, the culture medium used according to the invention comprises malt and/or yeast extract. According to a preferred embodiment, the mycelium used for step c) is concentrated. Preferably, the concentration of the mycelium used for step c) is between 5 and 15 g/l, preferably 6 to 12 g/l, very preferably 7 to 10 g/l.

It has been particularly noted that the production of (S)-gamma-lactone by the *Mortierella* strain is particularly promoted, in terms of stereoselectivity and in terms of yield, by the use of a swollen mycelium filled with inclusions as described above; in fact, the use of such a mycelium would make it possible to obtain a reaction product which has an optical rotation greater, in absolute value, than those of the prior art; furthermore, the yield obtained by means of the process according to the invention, and in particular by the use of a swollen mycelium filled with inclusions as described above, makes it possible to obtain yields greater than those of the prior art.

Step c) of the process consists in adding the substrate to the cell culture. According to the invention, the biological synthesis of gamma-undecenolactone involves any appropriate substrate, and preferably undecylenic acid or one of its esters. Among the other preferred substrates, mention may be made of all substituted derivatives of undecylenic acid or of its esters. Undecylenic acid and the methyl ester and ethyl ester of undecylenic acid are particularly preferred substrates. It goes without saying that the substrate can be any appropriate substrate, or a mixture of various appropriate substrates, in particular a mixture of undecylenic acid and of one or more of its esters.

According to an advantageous embodiment of the invention, the substrate is added to the mycelium according to a batchwise or fed-batch process. According to a preferred embodiment, the undecylenic acid is added as a mixture with an auxiliary product, for example an oil, in particular any conventional food oil such as soybean, maize, sunflower, or the like, or synthetic short-chain fatty acid triglycerides such as miglyol, preferably sunflower oil which is hydrogenated or rich in oleic acid, prior to it being brought into contact with the mycelium. The presence of the auxiliary product makes it possible in particular to greatly decrease the corrosive or toxic effect of the substrate, in particular of undecylenic acid. According to one embodiment of the invention, the synthesis according to the invention using the *Mortierella isabellina* strain is carried out in a medium free of mineral oil.

Advantageously, the substrate is added in concentrations of from 0.3 to 2.5 g/l/h. Advantageously, the amount of oil, preferably of plant oil, mixed with the substrate is from 100 to 500 g/l, preferably 150 to 300 g/l.

A source of sugar, preferably of glucose, is also added to the medium, at the same time as the substrate, so as to ensure that the energy needs of the cells are covered. Advantageously, the concentration of glucose added is from 0.3 to 0.4 g/l/h.

The pH can be adjusted, as needed, during the addition of the substrate and throughout the duration of the bioconversion that will follow, by means of the addition of any appropriate base. The pH should be between 4.5 and 8.5, preferably between 5.5 and 8, and preferably between 6 and 7.5.

The temperature is preferably maintained between 27 and 30° C., during the bioconversion. The duration of the bioconversion may be from 30 to 120 hours, preferably from 48 to 72 hours.

The bioconversion of the substrate to gamma-undecenolactone, covered in step d) of the process of the invention, is a step consisting of lactonization preceded by a reaction consisting of hydroxylation of the substrate at $C_4$, carried out by the strain. A source of oxygen is required in order for it to be possible for this hydroxylation to be carried out. This source of oxygen is preferably a gas containing oxygen, very preferably air or oxygen. The gas is dissolved in a relatively large amount in the reaction medium.

According to a preferred embodiment, and as is known in the prior art, antifoams, in particular silicone oils or polymers of polyethylene glycol esterified with fatty acids, are used to control the foam that may form during the bioconversion.

Once the bioconversion, i.e. the specific and stereo-selective hydroxylation at $C_4$, followed by the lactonization, has been carried out, step e) of the process consists in recovering the gamma-undecenolactone by extraction, the extraction of the gamma-undecenolactone being carried out by any appropriate means. Advantageously, the extraction of the gamma-undecenolactone is carried out by hydrodistillation, optionally followed by an esterification intended to subsequently eliminate the substrate which has not reacted.

Alternatively, the extraction of the gamma-undecenolactone is carried out by solvent extraction (cyclohexane, ethyl acetate), after acidification of the medium.

According to a variant of the process according to the invention, step e) of the process is not carried out, and instead, a step e') is carried out, which step consists in continuing the process at the end of step d) by means of an in situ reduction of the gamma-undecenolactone obtained, before extraction, so as to obtain, for example, the corresponding gamma-undecalactone. According to a specific embodiment, the reduction can be stopped so as to obtain a gamma-undecenolactone that has fewer unsaturations than that derived from the bioconversion of step d). According to this other embodiment, the process according to the invention is continued at the end of step d) by stopping the pH regulation of the fermenter, and adding an active dry yeast, which may be a baker's yeast, a wine-maker's yeast or a brewer's yeast, and a source of sugar, in particular of glucose, to the reactor. When the pH reaches the value of 5.5, it is regulated at 5.5 with an appropriate base, for example sodium hydroxide. The mixture is left to incubate in order for the reduction to take place, preferably for a period of 12 to 24 hours, and then the gamma-undecenolactone is extracted under the conditions described in step e). According to another variant, the gamma-undecenolactone can be reduced to gamma-undecalactone by means of a fresh culture of a reducing microorganism or a microorganism that is at least placed under reducing conditions, for example *Saccharomyces cerevisiae* or *Pichia etchelsii, Pichia pastoris, Hansenula polymorpha, Bacillus subtilis* or *Lactobacillus brevis*.

According to a specific embodiment of the invention, the reduction in step e') results in the production of gamma-undecalactone and this gamma-undecalactone corresponds to the formula:

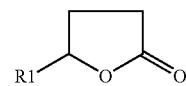

in which R1 is an optionally substituted $C_7$ alkyl group. The term "substituted alkyl" is intended to mean an alkyl, at least one carbon of which bears at least one substituent group. The term "substituent group" is intended to mean in particular a hydroxyl group, a keto group, a thiol group, an alkyl group or an alkenyl group.

According to a preferred embodiment of the invention, R1 is the group $C_7H_{13}$, very preferably $CH_2\!=\!CH\!-\!CH_2\!-\!CH_2\!-\!CH_2\!-\!CH_2\!-\!CH_2\!-\!$.

The gamma-undecalactone obtained according to this specific embodiment contains an asymmetrical carbon in position 4 which has the same configuration as that of the gamma-undecenolactone molecule from which it derives, since the reduction reaction does not modify the stereoisomerism of the molecule.

Step e') can also be carried out and makes it possible to obtain a more saturated (R)- or (S)-undecenolactone or an (R)- or (S)-gamma-undecalactone, depending on the stereochemistry of the gamma-undecenolactone obtained in step d).

These saturated lactones, the (R)-gamma-undecalactone and the (S)-gamma-undecalactone, can be used in the same applications as their unsaturated homologs: these lactones have odorant and gustative properties such that they can be used in all perfumery and food flavoring applications, in particular for the production of perfumes, of odorant substances, or of cosmetic or food compositions, or as a food additive.

For the purpose of the present invention, the term "perfumery" denotes not only perfumery in the usual sense of the term, but also the other fields in which the odor of products is important. This may involve perfumery compositions in the usual sense of the term, such as fragrancing bases and concentrates, eaux de Cologne, eaux de toilette, perfumes and similar products; topical compositions—in particular cosmetic compositions—such as face and body creams, talcum powders, hair oils, shampoos, hair lotions, bath salts and oils, bath and shower gels, toilet soaps, body antiperspirants and deodorants, shaving lotions and creams, soaps, creams, toothpastes, mouthwashes, ointments, and similar products; and maintenance products, such as softeners, detergents, washing powders, air fresheners, and similar products.

The term "odorant" is used to denote a compound which gives off an odor.

The term "food flavoring" is intended to mean any use of the compounds of the invention for the flavoring of any human or animal, liquid or solid food product, in particular drinks, dairy products, ice creams.

The gamma-undecenolactone, (R) or (S), or a mixture of (R) and (S), and also the gamma-undecalactone, (R) or (S), or a mixture of (R) and (S), can be used as perfuming compositions in order to contribute to providing exotic, floral or fruity notes, which has resulted in the applicant registering the trademark "Tropicalone®" given to the gamma-undecenolactone. According to the applications, the (S) enantiomer or the (R) enantiomer, or else a mixture of the 2 enantiomers in proportions determined by a person skilled in the art, will be used.

Preferably, the products according to the invention are used in amounts of between 0.0025% and 10% by weight relative to the total weight of the composition in which they are present. They may go to make up the composition of solids or of liquids, and in particular the composition of gels, creams, ointments and/or sprays.

The products according to the invention can also be used in a composition that is itself odorant, or in a composition in which the odorant agent is used to mask or neutralize certain odors.

Other characteristics and advantages of the present invention will emerge clearly upon reading the examples given hereinafter, which illustrate the invention without, however, limiting it.

EXAMPLE 1

Step a:—Selection of Strains

All the strains of the collection are first inoculated onto MGY agar medium and incubated for 72 h at 27° C.; these strains are subsequently inoculated into one-liter Erlenmeyer flasks containing 100 ml of 1× malt medium and incubated for 24 h at 27° C. The substrate, undecylenic acid, is then added to the culture medium (5 g/l in 10 doses) and the culture is maintained for a further 48 h to 120 h at 27° C.

After olfaction and analyses of the gamma-undecenolactone concentration in the media, the most advantageous strains are selected; this was the case for the *Mortierella isabellina* CBS 100559, *Mortierella isabellina* CBS 221.29, *Aspergillus oryzae* DSMZ 1861 and *Aspergillus oryzae* CBS 110.27 strains, which were subsequently used for the fermenter optimization trials.

EXAMPLE 1

Step b:—Preparation of Cell Cultures

The *Mortierella isabellina* CBS 100559, *Mortierella isabellina* CBS 221.29, *Aspergillus oryzae* DSMZ 1861 or *Aspergillus oryzae* CBS 110.27 strain (origin=tube frozen at −80° C.) is inoculated onto MGY agar and incubated at 27° C. for 30 minutes.

The above preculture is inoculated into 5 l of 1× malt medium in a 6 l fermenter:

| | |
|---|---|
| Malt extract: | 165 g |
| Yeast extract: | 25 g |
| H$_2$O qs: | 5 l |
| pH: | 6.5 |

*Mortierella Isabellina*

Incubation is carried out at 27° C., 500 rpm, 3.5 l/l/h of air, open pH, for 30 hours.

*Aspergillus Oryzae*

Incubation is carried out at 20° C., 500 rpm, 0.05 vvm of air, open pH, for 30 h and then at 25° C., 500 rpm, 0.05 vvm of air, open pH, for 24 hours. In both cases, a mycelium containing many large bulges full of inclusions (including peroxysomes) should be obtained.

125 l of 1.5× malt medium are then prepared in a 300 l fermenter:

| | |
|---|---|
| Malt extract: | 6.188 kg |
| Yeast extract: | 0.938 kg |
| H$_2$O qs: | 125 l |

The medium is sterilized for 40 minutes at 121° C. The fermenter and its parts are sterile and pressurized. The temperature is stable and regulated at 27° C. The pressure is flushed and an air flow rate of 3.5 l/l/h, i.e. approximately 0.6 m$^3$/h, is maintained. The base (10 N NaOH), the acid (85% H$_3$PO$_4$), the antifoam and the 6 l fermenter which serves as inoculum are sterily brought together. The agitation speed is adjusted to 325 rpm, the antifoam is initiated, and then the inoculum (5 l) is inoculated, open pH. The agitation speed is maintained at 325 rpm and the aeration is increased to 2.2 m$^3$/h (0.3 vvm). Growth is allowed to continue for 24 hours, so as to have approximately 10 g/l of mycelium on a dry weight basis: this mycelium should be "compot" and should consist of filaments comprising numerous bulges and swellings, without spores.

EXAMPLE 2

Steps c and d: Conversion of the Undecylenic Acid by the *Mortierella* sp. Strains Once the amount and the quality of mycelium have been achieved, the undecylenic acid is dispensed at the flow rate of 0.3 g/l/h for 6 h, and then at the flow rate of 0.53 g/l/h for 72 h: i.e. a total of 40 g/l. This undecylenic acid is dispensed as a mixture with hydrogenated sunflower oil (¼ acid-¾ oil); this oil is therefore dispensed at the flow rates of 0.9 g/l/h and then 1.53 g/l/h. Glucose is continuously dispensed, in parallel, at the flow rate of 0.36 g/l/h for 72 h. The pH is regulated at 7.5 throughout the duration of the fermentation, with 5 N NaOH. The speed is increased to 505 rpm and aeration is carried out at the flow rate of 1 vvm, i.e. 12 m$^3$/h. The conversion is pursued for 72 hours.

A production of 6.5 g/l of gamma-undecenolactone, the stereoisomerism of which is (S), is obtained.

EXAMPLE 3

Steps c and d: Conversion of the Undecylenic Acid by the *Aspergillus* sp. Strains Once the amount and the quality of the mycelium have been attained, the undecylenic acid is dispensed at the flow rate of 0.3 g/l/h for 6 h, and then of 0.53 g/l/h for 72 h: i.e. a total of 40 g/l. This undecylenic acid is dispensed as a mixture with hydrogenated sunflower oil (¼ acid-¾ oil). Glucose is continuously dispensed, in parallel, at the flow rate of 0.36 g/l/h for 72 h. The pH is regulated at 6.5 throughout the duration of the fermentation, with 5 N NaOH. Aeration is carried out at the flow rate of 0.5 vvm, i.e. 6 m$^3$/h. The conversion is pursued for 80 hours. A production of 0.5 g/l of gamma-undecenolactone, the stereoisomerism of which is (R), is obtained.

EXAMPLE 4

Step e: Extraction-Purification

Acidification at pH 1.5 is carried out with 3 l of 85% phosphoric acid. Heating is carried out at more than 100° C. for 30 minutes in order for the lactone to be essentially in its cyclized form and not in its open hydroxy acid form. The lactone is quantitatively determined, extraction solvent is added (preferably cyclohexane), and the mixture is stirred at ambient temperature for 1 hour. Centrifugation is carried out and the organic phase is recovered. The lactone is quantitatively determined. The solvent is concentrated and an oily "crude" is thus obtained. Vacuum distillation is carried out. The "deresined" lactone and an exhausted oil are obtained. Purification is subsequently carried out by fractionating the lactone under vacuum. A product that is >99% pure is obtained, which product is either gamma-undecenolactone (>99% S) if a strain of *Mortierella* sp. was used, or gamma-undecenolactone (>99% R) if a strain of *Aspergillus* sp. was used.

EXAMPLE 5

Step e': Reduction of Gamma-Undecenolactone to Gamma-Undecalactone

Instead of stopping the reaction, after the bioconversion of example 3, the process is continued as follows:

The fermenter pH regulation is stopped. 200 g/l of active dry yeast from commercial baker's yeast (i.e. 30 kg of yeast) and 100 g/l of glucose (i.e. 15 kg of dry-glucose or 30 kg of glucose syrup at 50%) are added to the medium. As soon as the pH reaches the value of 5.5, the pH is regulated at pH 5.5, with a 5 N NaOH base. Incubation is carried out for 12 to 24 h at 30° C., 325 rpm, air at 0.5 vvm. (S)-gamma-undecalactone or (R)-gamma-undecalactone are obtained, as appropriate. The extraction and the purification are then carried out in accordance with example 4 above.

EXAMPLE 6

Evaluation of the (S)-Gamma-Undecenolactone in Perfumery

The 99%-pure (S)-gamma-undecenolactone was tested on a sponge and in solution (of 5% in ethanol): the head gives the impression of lactonic aldehyde of gamma-undecalactone intreleven aldehyde type (IFF), and very powerful. The background is very natural, lactonic and very powerful pineapple flesh.

It was also tested in a formulation where it gives an interesting marine fruity note, for example in the following formula:

| | |
|---|---|
| Phenyl ethyl alcohol | 150 g |
| Calone | 1 g |
| Citronellol | 20 g |
| Dipropylene glycol | 50 g |
| Galaxolide | 200 g |
| Methyl dihydro jasmonate | 150 g |
| Helional | 15 g |
| Indole | 2 g |
| Beta-ionone | 15 g |
| IsoE super | 150 g |
| Lilial | 130 g |
| Linalol | 49 g |
| Melonal | 3 g |
| Methylionantheme | 15 g |
| Gamma-undecenolactone (Tropicalone ®) | 50 g |

EXAMPLE 7

Evaluation of the (S)-Gamma-Undecenolactone in Terms of a Food Flavoring

The 99%-pure (S)-gamma-undecenolactone was tested at 10 ppm in mineral water: it has a woody and fruity note very different from that given by any other lactone used up until now in formulation; by comparison with (R)-gamma-decalactone, with (R) delta-decalactone and with (R) delta-dodecalactone, at the same dosage (10 ppm), it has more of a coco flavor and is more woody with pineapple and passion fruit notes.

In sugary water (10 ppm), it also has notes with a milk-like, very fatty, sugary, sweet characteristic. Its potency at 10 ppm gives it an advantage in formulation due to its unique milk characteristic, concentrated milk tendency.

Also tested at 0.5 ppm and 1 ppm on a cream flavoring: it stands out better in the mouth at 0.5 ppm, giving a roundness to the cream and giving it a unique condensed milk-type characteristic.

EXAMPLE 8

Evaluation of the (S)-Gamma-Undecalactone in Terms of Food Flavoring

When compared at 99%-pure on a sponge with (R)-gamma-undecalactone, (S)-gamma-undecalactone gives less fatty, more natural and more "peachy" notes.

When evaluated at 10 ppm in mineral water, it gives a characteristic peach and apricot taste.

EXAMPLE 9

Evaluation of the (S)-Gamma-Undecalactone in a Food Flavoring Formulation

The addition of gamma-undecenolactone to an exotic fruit flavoring increases the "exotic" appreciation, for example in the following formula:

| | |
|---|---|
| Rose oxide | 10.4 g |
| Phenyl oxide | 10.4 g |
| Phenyl propyl aldehyde | 20.7 g |
| Neryl acetate | 0.30 g |
| Gamma-undecalactone | 1 g |
| Gamma-nonalactone | 1 g |
| Styrax | 6.2 g |
| Acetyl methyl carbinol | 10.4 g |
| Delta-dodecalactone | 10.4 g |
| Gamma-decalactone | 10.4 g |
| Caproic acid | 20.7 g |
| Furaneol | 21.75 g |
| Terpentine | 31.1 g |
| Hexyl alcohol | 41.5 g |
| Caryophyllene | 51.8 g |
| para-Cymene | 0.2 g |
| Citronellyl propionate | 6.2 g |

-continued

| | |
|---|---|
| Nerol | 20.7 g |
| Hexyl caproate | 20.7 g |
| Citral 1,3, cis-3-hexenol | 103.6 g |
| Triacetin | 599.25 g |
| Gamma-undecenolactone (Tropicalone ®) | 2.5 g |

Same effect in a passion fruit flavoring:

| | |
|---|---|
| Butyl alcohol | 1.00 g |
| Hexyl alcohol | 1.00 g |
| 2-Ethyl-1-hexanol | 1.60 g |
| Caprylic alcohol | 2.10 g |
| Damascenone | 3.10 g |
| Butyl butyrate | 4.70 g |
| Beta-ionone | 21 g |
| Cis-3-hexenyl acetate | 52.60 g |
| Heptyl butyrate | 78.8 g |
| Gamma-decalactone | 79 g |
| Caproic acid | 105 g |
| Butyl isovalerate | 105.10 g |
| Delta-nonalactone | 1.00 g |
| Hexyl caproate | 42 g |
| Essence orange brazil | 131.4 g |
| Butyl acetate | 1.00 g |
| Butyric acid | 1.60 g |
| Benzoic aldehyde | 52.60 g |
| Ethyl butyrate | 157.7 g |
| Cis-3-hexenol | 157.7 g |
| Gamma-undecenolactone | 2.5 g |

What is claimed is:

1. A gamma-undecenolactone corresponding to formula (I):

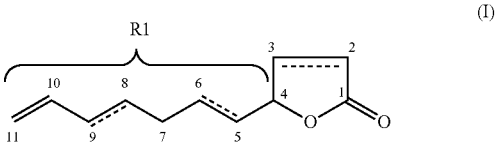

wherein each dashed line represents the position of a possible double bond.

2. The gamma-undecenolactone as claimed in claim 1, wherein the configuration at carbon 4 is (R).

3. The gamma-undecenolactone as claimed in claim 1, wherein the configuration at carbon 4 is (S).

4. The gamma-undecenolactone as claimed in claim 1, wherein the lactone ring is saturated and R1 is a $C_7H_{13}$ group.

5. A perfumery composition, comprising an undecenolactone as defined in claim 1.

6. A food composition, comprising an undecenolactone as defined in claim 1.

7. A food additive, comprising an undecenolactone as defined in claim 1.

* * * * *